United States Patent [19]

Muller et al.

[11] Patent Number: 5,584,295
[45] Date of Patent: Dec. 17, 1996

[54] SYSTEM FOR MEASURING THE PERIOD OF A QUASI-PERIODIC SIGNAL

[75] Inventors: Jeremy L. Muller, Pelham, N.H.; Robert G. Hohlfeld, Arlington, Mass.

[73] Assignee: Analogic Corporation, Peabody, Mass.

[21] Appl. No.: 523,043

[22] Filed: Sep. 1, 1995

[51] Int. Cl.[6] .................................................. A61B 8/00
[52] U.S. Cl. .................................................. 128/661.07
[58] Field of Search .................... 128/660.01, 661.07, 128/661.08, 661.09, 696, 698; 395/2.4, 2.45, 2.46; 364/413.25; 382/170

[56] References Cited

U.S. PATENT DOCUMENTS 4,453,550  6/1984  Flax ................................. 128/660.01

Primary Examiner—George Manuel
Attorney, Agent, or Firm—Lappin & Kusmer LLP

[57] ABSTRACT

The disclosed system for measuring the periodic content of an input signal includes an autocorrelation function generator for generating a sequence of autocorrelation functions. Each of the autocorrelation functions is representative of an autocorrelation function of a portion of the input signal. The system further includes a temporal filter for filtering the autocorrelation functions and thereby generating a lag histogram.

In other forms the system may comprise a fetal heart rate monitor for measuring the heart rate of a fetus in vivo. The monitor generates a lag histogram and uses the lag histogram for stabilizing the determination of the fetal heart rate.

25 Claims, 5 Drawing Sheets

SYSTEM FOR MEASURING THE PERIOD OF A QUASI-PERIODIC SIGNAL

FIELD OF THE INVENTION

The present invention relates generally to systems for measuring the period of a quasi-periodic signal. More particularly, the invention relates to systems which generate and use a lag histogram to measure the period of a quasi-periodic signal.

BACKGROUND OF THE INVENTION

As is well known, systems for measuring the periods of periodic and quasi-periodic signals have many useful applications. For example, such systems are useful for measuring the angular velocity of rotating machinery. Such systems are also useful in the medical arts for measuring biorhythmic parameters of a patient such as the heart beat, and such systems also have many other applications.

The well known autocorrelation function is often used to measure the periodic content of signals. The autocorrelation function has many well known mathematical properties and formulations (as are described in detail for example in Oppenheim & Schafer, *Discrete Time Signal Processing*, Prentice Hall Signal Processing Series, 1989) and one example of a formula for generating the autocorrelation function is given by Equation (1)

$$ACF(\tau) = \lim_{WIDTH \to \infty} \frac{1}{WIDTH} \int_{-WIDTH/2}^{WIDTH/2} v(t)v(t+p)dt \quad (1)$$

in which v(t) is an input signal and ACF(τ) is the autocorrelation function of the input signal. Similar formulas are also well known for generating the autocorrelation function from a discrete sampled input signal v(n). As can be seen from Equation (1), for each value of τ, the autocorrelation function may be thought of as a product of the input signal v(t) with a copy of itself that has been delayed in time by an amount τ. The autocorrelation function is thus a function of this delay, and the variable τ is often referred to as the "delay" or the "lag".

The autocorrelation function has a peak value for τ equal to zero, and if the input signal v(t) is periodic with a period of T, then the autocorrelation function will also have peak values for τ equal to integer multiples of T. The period of the input signal v(t) may therefore be determined by locating the peaks of the autocorrelation function, since the peaks are spaced apart by an amount of lag equal to the period T, and further, the location of the first peak for τ greater than zero (i.e., at τ=T) is representative of the period.

The averaging properties of the autocorrelation function make it particularly useful for determining the period of signals having relatively low signal-to-noise ratios. Even if the input signal has a low signal-to-noise ratio, the autocorrelation function will still have peaks at values of τ equal to integer multiples of T, since for these values all the periodic components of the input signal "line up" coherently and make a large contribution to the autocorrelation function, whereas the noise components which are generally random and therefore do not line up coherently make a comparatively smaller contribution to the autocorrelation function. However, the presence of noise may introduce "false" peaks and may also reduce the amplitude of the "true" peaks (i.e., the peaks that are representative of the periodic content of the signal).

The autocorrelation function has many advantageous idealized mathematical properties, however, several problems are encountered when implementing systems which use the autocorrelation function to measure the periodic content of "real world" naturally occurring signals. One such problem relates to the size of the interval over which data is collected to compute the autocorrelation function. Generally, it is never practical to approach an infinitely long data collection interval, e.g., in Equation (1) WIDTH is generally set to a large constant rather than being allowed to approach infinity. Using a finite data collection interval destroys some of the desirable statistical properties of the autocorrelation function. However, as long as the data collection interval is chosen to be relatively large so that the autocorrelation function is computed using many periods of the input signal, the autocorrelation function still provides relatively good noise rejection (i.e., the false peaks have relatively low amplitude) and the peaks in the autocorrelation function will still correspond to the period of the input signal. However in general, as the size of the data collection interval decreases, the autocorrelation function becomes increasingly sensitive to noise, and the confidence that any peak in the autocorrelation function actually corresponds to the period of the input signal decreases.

Another problem with the autocorrelation function relates to the quasi-periodic nature of most signals of interest. Very few signals occurring in the real world are perfectly periodic. Rather, most signals that are considered to be periodic, such as a signal representative of a heart rate, have periods that actually vary over time, and are therefore quasi-periodic signals. Provided that the deviation from periodicity in a signal is not too extreme, it is meaningful to consider a quasi-periodic signal as having a period which is variable in time. It is often desirable to be able to measure the instantaneous value of the period of a quasi-periodic signal. For example, it is desirable for a heart monitor to continuously display the instantaneous value of the heart rate and to track the heart rate as it varies over time. However, since the autocorrelation function is generated essentially by an averaging process, autocorrelation functions generated using large data collection intervals are not well suited to making such instantaneous measurements.

Quasi-periodic signals may be characterized by a parameter referred to as the "coherence time" which describes the time required for a signal to change its frequency and phase information. The coherence time is reflected in the autocorrelation function of a quasi-periodic signal. The peak at zero lag (i.e., τ=0) is the strongest, or maximum amplitude, peak in the autocorrelation function of a quasi-periodic signal. Successive peaks at increasing multiples of the period are increasingly weaker, and as the lag value approaches the coherence time, the peaks in the autocorrelation function approach the "noise floor" generated by the non-periodic components of the signal and the noise. Further, the peaks in the autocorrelation function of a quasi-periodic signal, apart from the zero lag peak, are both broadened and diminished in amplitude by the variability in the period as compared to the peaks in the autocorrelation function of a truly periodic signal. Generating the autocorrelation function is essentially an averaging process, and the peaks in the autocorrelation function of a quasi-periodic signal essentially represent an average over the data collection interval of the signal's time-varying period, and are therefore not representative of the instantaneous value of the period.

Since the peaks of the autocorrelation function represent an average of the period of the signal over the data collection interval, one way to make the peaks more representative of the instantaneous value of the period is to decrease the size of the data collection interval. However, as was discussed above, the autocorrelation function becomes increasingly sensitive to noise as the size of the data collection interval is decreased. There is therefore a tradeoff between noise rejection and the ability to measure the instantaneous value of the period when using the autocorrelation function.

Another problem with quasi-periodic signals, such as signals representative of a heart rate, is that the periodic components of these signals sometimes vanish for several periods and then reestablish themselves. Such occurrences are commonly referred to as "data dropout", and autocorrelation functions computed over relatively small data collection intervals are particularly sensitive to such data dropouts.

In general, prior art systems which use the autocorrelation function to measure the instantaneous value of the period of a quasi-periodic signal include a peak detector for locating peaks in the autocorrelation function. However, due to the problems discussed above, as well as other problems, the locations of the peaks do not correspond exactly to the instantaneous value of the period. Prior art systems therefore generally employ several ad hoc techniques to convert the location of the peaks to an estimate of the period. However, such ad hoc techniques are generally ineffective at remedying the shortcomings of the autocorrelation function. There is therefore a need for improved systems and techniques for accurately estimating the instantaneous value of the period of a quasi-periodic signal.

OBJECTS OF THE INVENTION

It is an object of the present invention to substantially reduce or overcome the above-identified problems of the prior art.

It is a further object of the present invention to provide a system for measuring the periodic content of an input signal, including a device for generating a sequence of autocorrelation functions representative of respective portions of the input signal and a device for generating a lag histogram by temporally filtering the sequence of calculations of autocorrelation functions.

Still another object of the present invention is to provide a system including a single pole filter for filtering the autocorrelation functions to generate the lag histogram.

Yet another object of the present invention is to provide a system including an adaptive filter for filtering the sequence of autocorrelation functions to generate the lag histogram.

And another object of the present invention is to provide an adaptive filter that varies adaptively as a function of the zero lag peaks of the autocorrelation functions.

It is a further object of the present invention to provide a device for locating a main peak in the lag histogram, the main peak being the largest peak in the lag histogram for a positive value of the lag.

Still another object of the present invention is to provide a fetal heart rate monitor including means for generating a lag histogram.

Yet another object of the present invention is to provide a fetal heart rate monitor including a data sampler.

And another object of the present invention is to provide a fetal heart rate monitor including a band pass filter for filtering the output signal generated by the data sampler.

It is a further object of the present invention to provide a multi-channel data sampler for generating sampled signals at different resolutions.

Still another object of the present invention is to provide a system including a device for generating an autocorrelation function so that at any point in time the autocorrelation function is representative of an autocorrelation function of a portion of an input signal, and including a device for generating the lag histogram from the autocorrelation function so that transitory features in the autocorrelation function are suppressed in the lag histogram and temporally stable or consistent features in the autocorrelation function are emphasized in the lag histogram.

Yet another object of the present invention is to provide a system that generates the lag histogram by temporally filtering portions of the autocorrelation function.

SUMMARY OF THE INVENTION

These and other objects are provided by an improved system for measuring the periodic content of an input signal. The system includes an autocorrelation function generator for generating a sequence of autocorrelation functions, each of a portion of the input signal. The system further includes a temporal filter for generating a lag histogram by temporally filtering the autocorrelation functions. In other aspects, the invention provides an improved fetal heart monitor for monitoring the heart beat of a fetus in vivo. The monitor uses the lag histogram to stabilize the determination of the fetal heart rate.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be had to the following detailed description taken in connection with the accompanying drawings in which the same reference numerals are used to indicate the same or similar parts wherein.

DETAILED DESCRIPTION OF THE DRAWINGS

Figure 1:
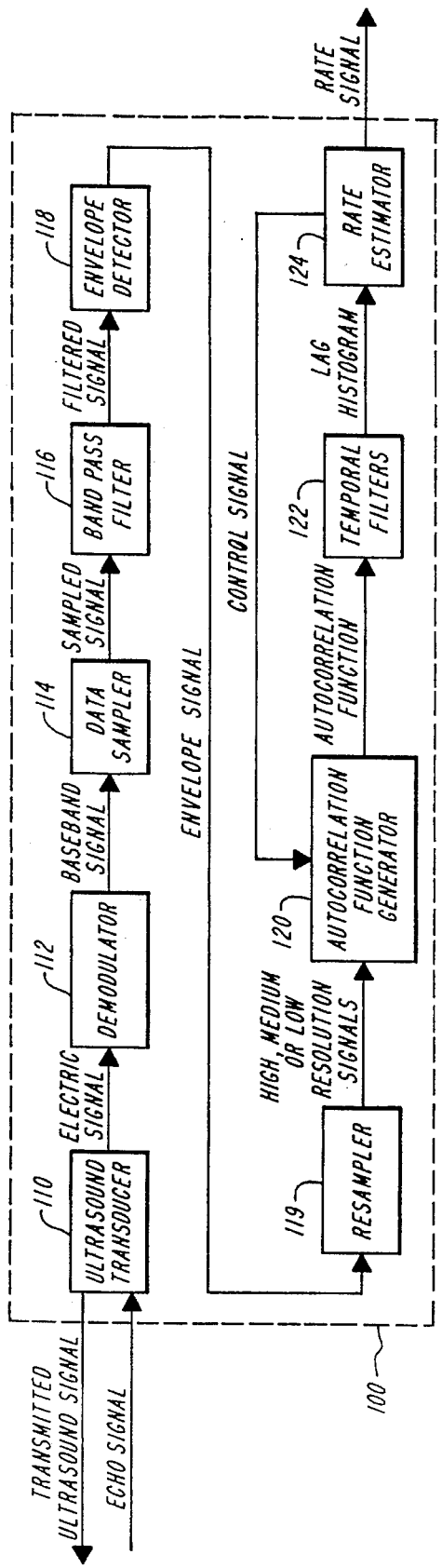
FIG. 1 shows a block diagram of a fetal heart monitor constructed according to the invention.

FIG. 1 shows a block diagram of a Doppler ultrasound fetal heart rate monitor 100 constructed according to the invention used for measuring the heart rate of a fetus in vivo. As will be discussed further below, rather than simply using the peaks of the autocorrelation function for determining the period of the fetal heart rate as in the prior art, monitor 100 generates a lag histogram from the autocorrelation function and uses the lag histogram to stabilize the estimation of the heart rate.

Monitor 100 includes an ultrasound transducer 110, a demodulator 112, a data sampler 114, a band pass filter 116, an envelope detector 118, a resampler 119 preferably in the form of a decimator, an autocorrelation function generator 120, a temporal filter 122, and a rate estimator 124. Ultrasound transducer 110 may be implemented as a single transducer or alternatively as an array of transducers as is well known. In operation, transducer 110 is positioned adjacent a mother's abdomen where it generates a transmitted ultrasound signal which propagates into the mother's body. As is well known, portions of the transmitted ultrasound signal are reflected by the fetus and by other structures in the mother's body and the portions reflected by moving structures are also Doppler shifted. Portions of the Doppler shifted ultrasound reflections are then received by transducer 110, and these reflections are referred to as the echo signal. Transducer 110 generates an electric signal representative of the echo signal and applies this electric signal to the input of demodulator 112. The latter demodulates the electric signal using known techniques and thereby generates a baseband signal representative of the echo signal. Data sampler 114 samples the baseband signal at one or more selected sampling frequencies thereby generating a sampled signal which is applied to the input of band pass filter 116. The latter receives and filters the sampled signal with a pass band that passes all frequencies in the range of possible fetal heart beats thereby generating a filtered signal. The filtered signal is applied to the input of envelope detector 118 which generates an envelope signal representative of the envelope of the filtered signal. The resampler 119 resamples the output of the envelope detector 118 at one or more selected sampling rates, preferably at three rates representing high, medium and low resolution. Autocorrelation function generator 120 receives the resampled envelope signal and generates therefrom an autocorrelation function which is applied to the input of temporal filter 122. As described below, where generator 120 provides signals of different resolutions a separate temporal filter can be provided for each resolution. Temporal filter 122 generates a lag histogram from the autocorrelation function and applies the lag histogram to the input of rate estimator 124. Rate estimator 124 then generates a rate signal representative of the instantaneous value of the fetal heart rate, and the rate signal may be used, for example, to drive a display (not shown). Rate estimator 124 may also generate a control signal used to control autocorrelation function generator 120.

Transducer 110 and demodulator 112 operate in a conventional fashion so that the baseband signal applied to data sampler 114 is representative of a baseband version of the Doppler shifted ultrasound echo signal. In the preferred embodiment of system 100 the data sampler data sampler 114, for example a decimator, samples at the highest expected frequency (for example, 2.6 KHz for single fetus operation and 1.3 KHz for twin fetuses operation). Band pass filter 116 is preferably implemented as a digital band pass filter, having a pass band in the range, for example, of 80 to 300 Hz, so that all signals in the frequency range of expected fetal heart beats are received. Envelope detector 118 preferably takes the absolute value of each sample of the filtered signals and then low pass filters the sequences of absolute value samples to generate the envelope signals. Thus, band pass filter 116 samples before the decimation sampling by the resampler 119. Resampler 119 is preferably implemented as a three channel device, having a low resolution channel, a medium resolution channel, and a high resolution channel. Resampler 119 generates low resolution, medium resolution, and high resolution sampled signals by sampling the baseband signal at sampling frequencies $f_1$, $f_2$, and $f_3$, respectively, where $f_3$ is greater than $f_2$ and $f_2$ is greater than $f_1$. In one preferred embodiment the sampling frequencies are chosen so that $f_3$ equals two times $f_2$ and so that $f_2$ equals two times $f_1$. For single fetus operation the decimation rates for $f_3$:$f_2$:$f_1$ are by factors of 2:4:8, while for twins the decimation rate for $f_3$:$f_2$:$f_1$ is 1:2:4. Thus, for example, for twins the preferred choice for the sampling frequencies is set so that $f_1$ equals 325.5 Hz, $f_2$ equals 651 Hz, and $f_3$ equals 1302 Hz.

As will be discussed further below, autocorrelation function generator 120 may use the low, medium, or high resolution envelope signal to generate the autocorrelation function, and the choice of resolution is controlled by rate estimator 124 via the control signal. Generator 120 preferably uses a data collection interval of between two and three beats worth of data to generate the autocorrelation function. Due to fetal physiology, fetal heart beats are normally in the range between about 50 to 240 beats per minute, and in the preferred embodiment, system 100 may accurately measure fetal heart rates between 50 and 240 beats per minute. This range is preferably divided into low, medium, and high ranges corresponding to the low, medium, and high resolution sampled signals, respectively. Subdividing the range in this manner reduces the data storage capacity used in system 100. This is so because whereas two to three beats near the top of the range (e.g., near 200 beats per minute) correspond to approximately 0.9 seconds of data, or about a thousand samples of the high resolution sampled signal, two to three beats near the bottom of the range (e.g., near 50 beats per minute) correspond to approximately three beats worth of data (i.e., about 3.6 seconds of data), although only two beats worth of data is usually sufficient, or about five thousand samples of the high resolution sampled signal and only about a twelve hundred and fifty samples of the low resolution sampled signal (where the ratio of high resolution data to low resolution data is about 4:1). Generator 120 preferably uses the high resolution signals for generating the autocorrelation functions when the fetal heart rate is near the top of the range, however, when the fetal heart rate is near the bottom of the range, the low resolution signals provide sufficient sampling for generation of an accurate autocorrelation function, so the additional samples of the high resolution signals need not be stored. Therefore to reduce the data storage requirements, generator 120 preferably uses the low resolution envelope signal when measuring heart rates near the bottom of the range, the medium resolution envelope signal when measuring heart rates near the middle of the range, and the high resolution envelope signal when measuring heart rates near the top of the range. Thus, for the example given, at 50 beats per minute (BPM) the maximum number of samples at the lowest rate is 1024.

Those skilled in the art will appreciate that dividing the ranges in this manner is useful for reducing data storage, however, other embodiments of system 100 may only use one sampling frequency and therefore only single channel devices for resampler 119, and filters 122. Still other embodiments may use other numbers of sampling frequencies, such as two, or four sampling frequencies, and generate corresponding numbers of different resolutions of the envelope signal.

Figure 2:
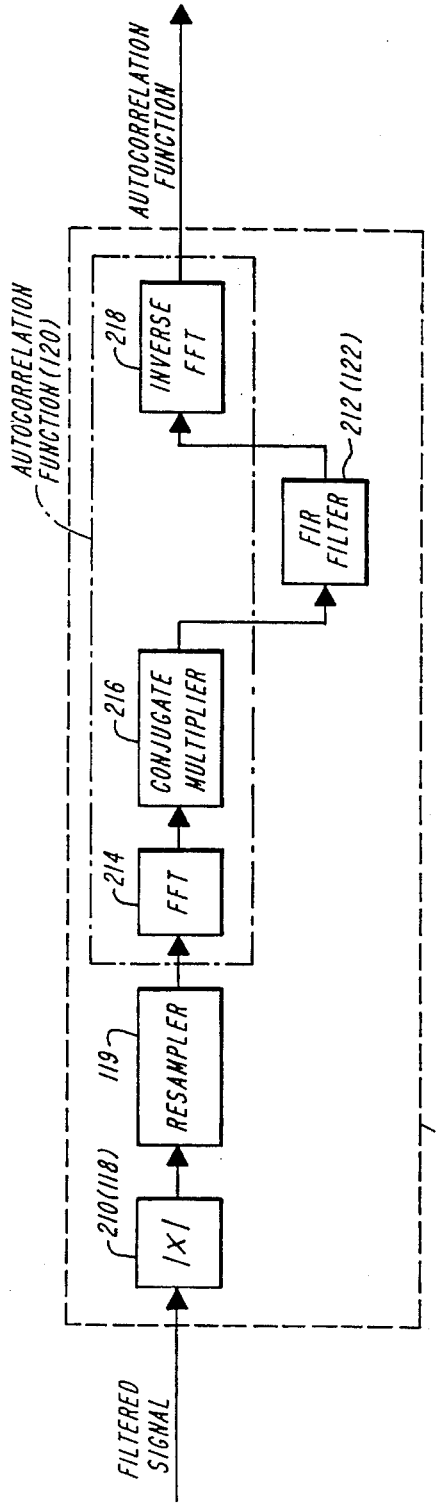
FIG. 2 shows in detail a block diagram of one embodiment of the envelope detector and autocorrelation function generator shown in FIG. 1.

The autocorrelation function generator 120 may use any one of the many known techniques for generating the autocorrelation function. However, in the preferred embodiment, generator 120 uses Fourier transform techniques of zero-filled circular autocorrelation to simulate a linear autocorrelation to generate the autocorrelation function, and moreover, in the preferred embodiment generator 120 and envelope detector 118 are implemented in a distributed fashion. FIG. 2 shows a block diagram of the preferred distributed embodiment of envelope detector 118 and autocorrelation function generator 120. In this embodiment, envelope detector 118 includes an absolute value detector 210, and a finite impulse response (FIR) filter 212, and autocorrelation function generator 120 includes a fast Fourier transform (FFT) device 214, a conjugate multiplier 216, and an inverse FFT device 218.

Absolute value detector 210 receives the filtered signal and generates a rectified signal that is applied to the input of FFT device 214. Every sample in the rectified signal is equal to the absolute value of a corresponding sample in the filtered signal applied to the input of detector 210. Detector 210 essentially acts as a digital full wave rectifier and rectifies the filtered signal. FFT device 214 generates a signal representative of the fast Fourier transform of the rectified signal, and applies this signal to the input of conjugate multiplier 216. The latter multiplies this signal by a well known conjugate signal so as to generate a frequency domain signal representative of the autocorrelation function of the rectified signal. FIR filter 212, which is a frequency domain implementation of a low pass filter, receives this frequency domain signal and generates a low pass filtered signal which is then applied to inverse FFT device 218. The latter takes the inverse FFT of the signal applied to its input and thereby generates the autocorrelation function.

As those skilled in the art will appreciate, FFT device 214, conjugate multiplier 216, and inverse FFT device 218 form an autocorrelation function generator. In a functionally equivalent implementation to the one shown in FIG. 2, FIR filter 212 is implemented as a time domain filter and is positioned between detector 210 and FFT device 214 rather than between conjugate multiplier 216 and inverse FFT device 218. In such an arrangement, the envelope detector is not distributed with the autocorrelation function generator. However, FIR filter 212 is more easily implemented as a frequency domain filter, and it is therefore preferred to implement envelope detector 118 and autocorrelation generator 120 in the distributed fashion shown in FIG. 2.

System 100 preferably generates the autocorrelation function at each of a sequence of times. For example, at time $t_1$ generator 120 generates an autocorrelation function $ACF(t_1, \tau)$, and at time $t_2$ generator 120 generates an autocorrelation function $ACF(t_2, \tau)$, and so on. Preferably the interval between generating successive autocorrelation functions (i.e., the interval between $t_1$ and $t_2$) is not greater than about 0.4 seconds. Each of the autocorrelation functions is generated using a data collection interval that includes approximately between two and three periods of data, so for example, the signal $ACF(t_1, \tau)$ is generated using samples of one of the filtered signals from time $t=t_1-xT$ to time $t=t_1$, where T is the period of the fetal heart rate and x is a number between two and three.

Temporal filter 122 generates the lag histogram by temporally filtering the autocorrelation function and as will be discussed further below, the autocorrelation functions used to generate the lag histogram are preferably generated from the low resolution sampled signal. Whereas prior art systems typically locate the peaks of the autocorrelation function and then discard the rest of the information contained in the autocorrelation function, system 100 preserves all the information in the autocorrelation function by using temporal filter 122 to generate the lag histogram. In one preferred form, temporal filter 122 uses a single pole filter and generates the lag histogram according to Equation (2):

$$LH(t_n,\tau)=(1-\alpha)LH(t_{n-1},\tau)+\alpha ACF(t_n,\tau) \qquad (2)$$

in which $LH(t_n, \tau)$ is the lag histogram at time $t_n$ and $\alpha$ is a filter coefficient which may be a constant or may be adaptively determined, although as those skilled in the art will appreciate, other filters may also be used.

Both the lag histogram and the autocorrelation function are applied to rate estimator 124 which as will be discussed further below uses both signals to generate the rate value which is representative of the fetal heart rate. Rate estimator 124 also generates the control signal for controlling autocorrelation function generator 120.

Figure 3A:
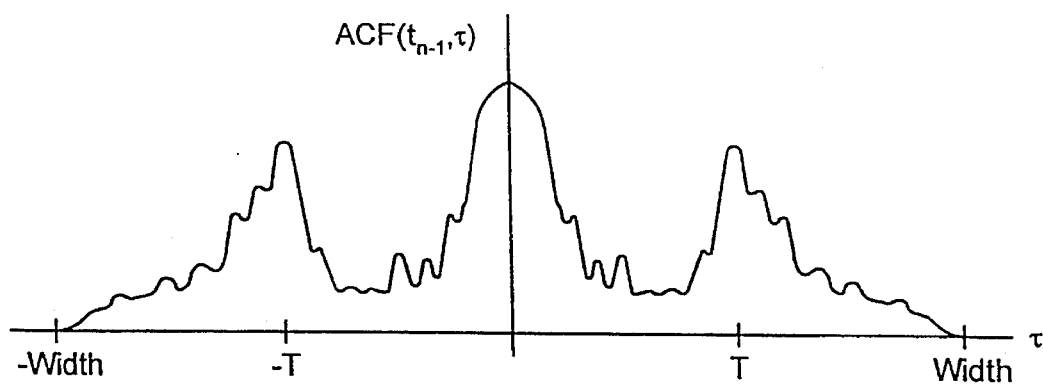
FIGS. 3A–3C are graphs illustrating the general form of autocorrelation functions generated by the autocorrelation function generator shown in FIG. 1.
Figure 3B:
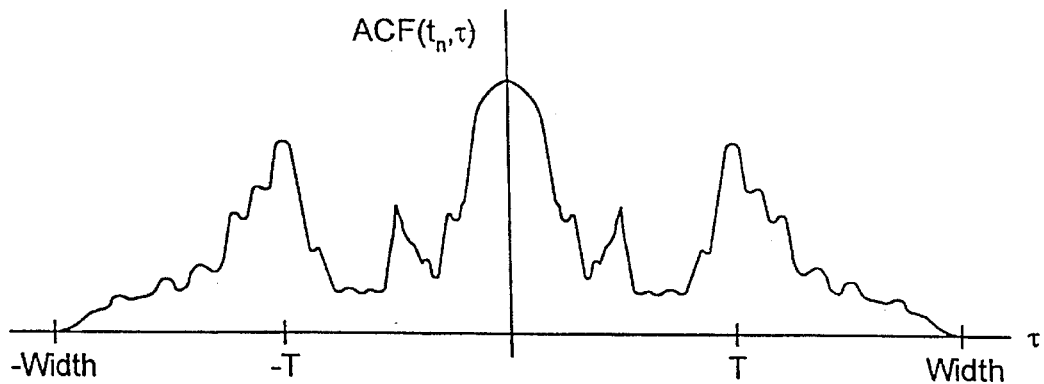
Figure 3C:
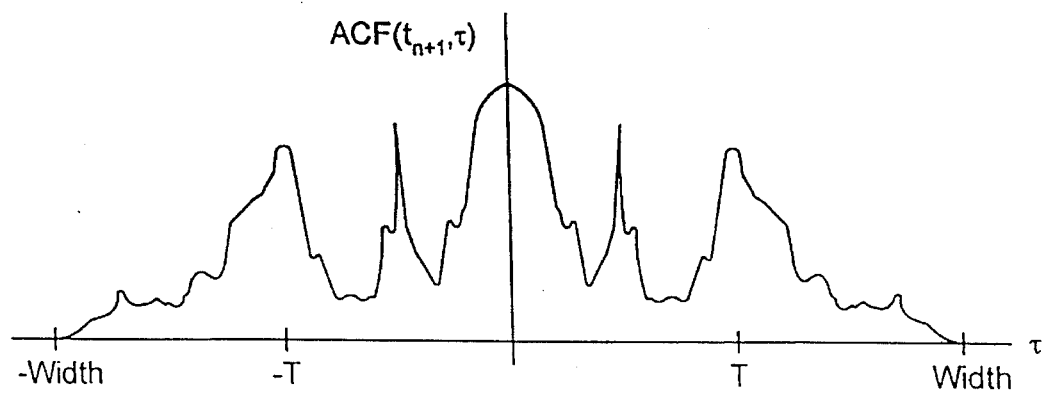

FIGS. 3A–C are graphs showing examples of autocorrelation functions generated by generator 120 at times $t_{n-1}, t_n$, and $t_{n+1}$, respectively. Those skilled in the art will appreciate that FIGS. 3A–C are not actual autocorrelation functions and are merely illustrative of the general form of the autocorrelation functions. When generator 120 uses a data collection interval of size WIDTH, the autocorrelation functions have a value of zero for $\tau$ greater than WIDTH and for $\tau$ less than minus WIDTH. Preferably WIDTH is selected to be between approximately two and three periods of the fetal heart rate. The autocorrelation functions have a maximum amplitude peak at $\tau$ equal to zero, and in general the next largest peaks are at $\tau$ equal to plus and minus T (where T is the period of the fetal heart rate). However, as shown in FIG. 3C, the autocorrelation functions will occasionally contain one or more false peaks that may be larger than the true peaks at $\tau$ equal to plus and minus T. Further, as was discussed above, the location of the true peaks drift along the $\tau$ axis as the period of the fetal heart rate fluctuates over time, and occasionally, the true peaks may vanish for one or more periods. Prior art systems generally detect the peaks and then discard the rest of the autocorrelation function, and such systems are therefore easily misled by the presence of false peaks and events such as data dropout and therefore generally provide only a relatively unreliable estimate of the fetal heart rate.

Figure 4:
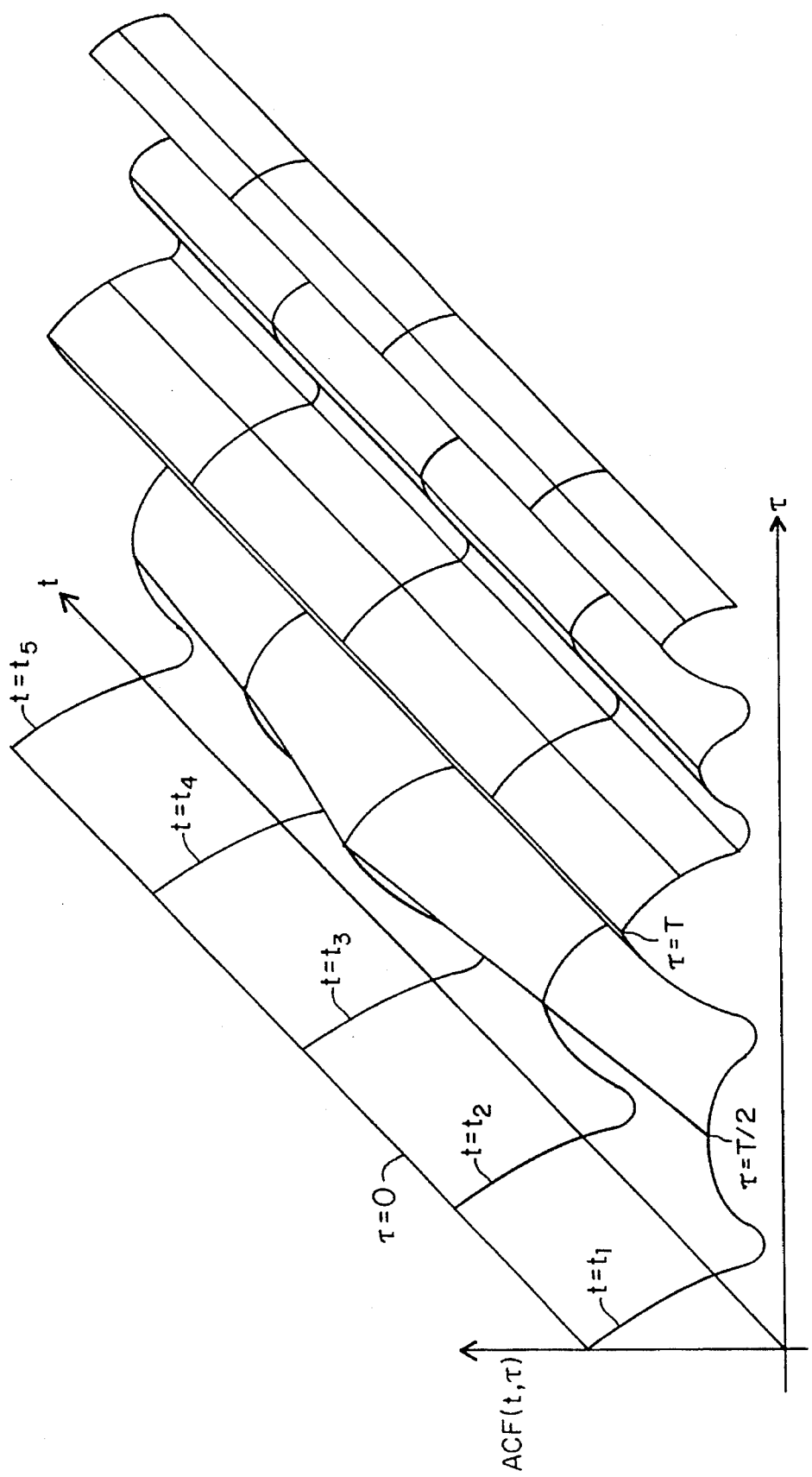
FIG. 4 is a graph illustrating a three dimensional representation of a time history of autocorrelation functions which may be generated by the autocorrelation function generator shown in FIG. 1.

In distinction from the prior art, system 100 preserves all the information in the autocorrelation functions by generating the lag histogram. FIG. 4 shows a graph illustrating the evolution of the autocorrelation functions over time for positive values of $\tau$. FIG. 4 is a three-dimensional representation of the autocorrelation functions in which the amplitude of the signals extend along the vertical axis, the lag $\tau$ extends along the horizontal axis, and time t extends along a diagonal axis representative of an axis perpendicular to the vertical and horizontal axes. As shown in FIG. 4, false peaks which occasionally appear in the autocorrelation function, such as the false peak at time $t=t_3$, are generally only transitory features and therefore appear as "bumps" extending along the time axis, whereas the true peaks at lag value $\tau=T$ tend to be temporally stable features and therefore appear as ridges extending along the time axis. Since filter 122 generates the lag histogram by temporally filtering the autocorrelation functions, the lag histogram tends to suppress transitory features of the autocorrelation functions (such as false peaks) and tends to preserve temporally stable features of the autocorrelation functions such as the true peaks. The lag histogram is therefore able to provide stability to the determination of the period.

As was stated above, the value of the filter coefficient $\alpha$ used in Equation (2) may be a constant, such as 0.2, or may be adaptively determined. In one preferred form, temporal filter 122 is an adaptive filter that has a relatively slow rise time and a relatively fast decay. The relatively slow rise time insures that the lag histogram suppresses false peaks and will only respond to new peaks if they are consistently present over a relatively long time. The relatively fast decay insures that peaks in the lag histogram decay relatively quickly unless their corresponding peaks in the autocorrelation functions remain relatively temporally stable.

One preferred form of temporal filter 122 generates the filter coefficient $\alpha$ so that it is a function of the value of the zero lag peak of the current autocorrelation function (i.e., the current value of the peak at $\tau=0$ of the autocorrelation function). The zero lag peak is indicative of the overall signal strength of the autocorrelation function, and in general a sudden increase in the zero lag peak is indicative of a sudden increase in noise (which may be caused by numerous events such as by an unwanted movement of the transducer 110, or by movement of the mother such as is caused during a cough or a sneeze, or by movement of the fetus such as "kicking"). So when there is a sudden change in the value of the zero lag peak it is preferable to decrease $\alpha$ so that the current autocorrelation function makes only a small contribution to the lag histogram. Thus, the filter is adaptive so that when the differences are large $\alpha$ is set for a slow response, while for large differences $\alpha$ is set for a fast response. The time constant for the average of the filter therefore provides a slow rise and rapid fall time so that many artifacts will result in a slow rise time to change the value of the autocorrelation function slowly, while removal of the artifacts will result in a fast response of the autocorrelation function.

Figure 5:
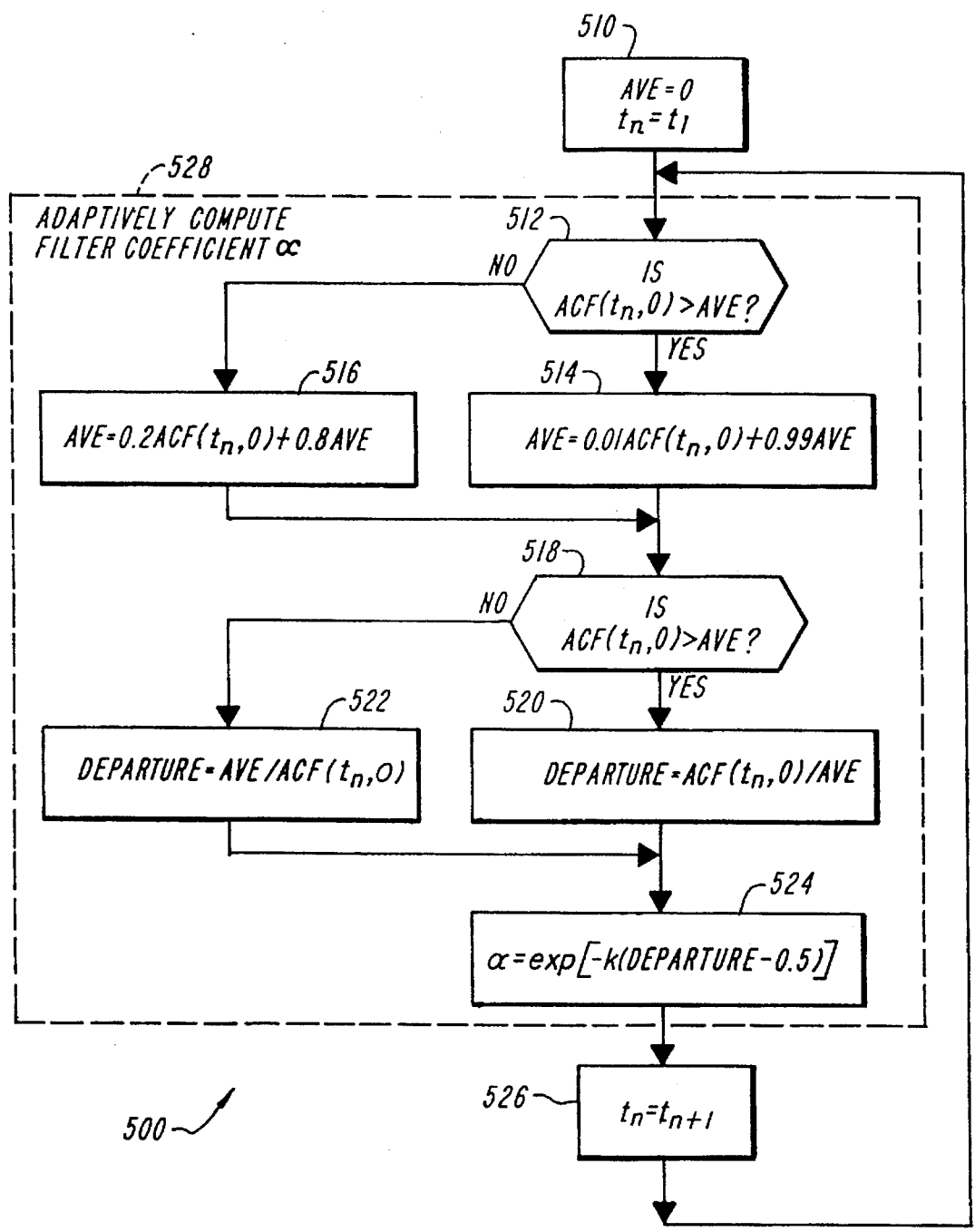
FIG. 5 shows a flow chart illustrating a method which may be used by the autocorrelation function generator shown in FIG. 1 for adaptively determining a filter coefficient.

FIG. 5 shows a flow chart illustrating one method 500 that temporal filter 122 may use to generate the filter coefficient $\alpha$. The first step in method 500 is an initialization step 510 in which the variables used are set to initial values. Specifically, a variable AVE is set equal to zero, and the variable $t_n$ is set equal to $t_1$ (i.e., the variable $t_n$ is set equal to the time at which the first autocorrelation function $ACF(t_1,\tau)$ is generated). Next a comparison step 512 is executed in which the current value of the zero lag peak (i.e., $ACF(t_n,0)$) is compared to the value of AVE. If the current value of the zero lag peak is greater than the value of AVE, then an update step 514 is executed and otherwise an update step 516 is executed. In update steps 514, 516 the value of AVE is updated using the current value of the zero lag peak and the current value of AVE. If the zero lag peak is greater than AVE, then AVE is updated using only a small percentage of the zero lag peak (i.e., the new value of AVE is set equal to $0.01ACF(t_n,0)+0.99$ times the old value of AVE), and if the zero lag peak is not greater than AVE, then AVE is updated using a larger percentage of the zero lag peak (i.e., the new value of AVE is set equal to $0.2ACF(t_n,0)+0.8$ times the old value of AVE). Those skilled in the art will appreciate that AVE is essentially a "time weighted average" of the zero lag peak, and steps 512, 514, and 516 essentially comprise a single pole adaptive filter with a relatively slow rise time and a relatively fast decay used for generating AVE. Following execution of either of steps 514, 516 another comparison step 518 is executed in which the current value of the zero peak lag is compared to the newly updated value of AVE. If the value of the zero peak lag is greater than AVE than an update step 520 is executed and otherwise an update step 522 is executed. Steps 520, 522 each compute the value of a variable DEPARTURE and DEPARTURE is computed so that it has a minimum value of unity and the amount by which DEPARTURE exceeds unity is representative of the departure of the current value of the zero lag peak from the time weighted average value of the zero lag peak (i.e., the amount by which $ACF(t_n,0)$ differs from AVE). When step 520 is executed, DEPARTURE is set equal to the current zero lag peak $ACF(t_n, 0)$ divided by the value of AVE, and when step 522 is executed, DEPARTURE is set equal to the value of AVE divided by the current zero lag peak $ACF(t_n, 0)$. Following the execution of either of steps 520, 522 an update step 524 is then executed. In step 524, the value of the filter coefficient $\alpha$ which is used in Equation (2) is calculated, and $\alpha$ is set equal to $e^{-k(DEPARTURE-0.5)}$. Since DEPARTURE has a minimum value of unity, $\alpha$ has a maximum value of $e^{(0.5k)}$, and as DEPARTURE increases, the value of $\alpha$ decreases. This insures that the autocorrelation functions which may contain artifacts do not contribute heavily to the lag histogram. Following execution of step 524, an incrementing step 526 is executed in which the variable $t_n$ is updated and then step 512 and all succeeding steps are then reexecuted using the new value of $t_n$ (i.e., the steps are then reexecuted so that the filter coefficient $\alpha$ may be calculated for use with the next generated autocorrelation function).

Method 500 may be considered as including initialization step 510, incrementing step 526, and a core step 528, where core step 528 includes steps 512, 514, 516, 518, 520, 522, and 524, and core step 528 essentially includes the core of the procedure for adaptively computing the filter coefficient $\alpha$. FIG. 5 illustrates one method that temporal filter 122 may use for adaptively determining $\alpha$, however, those skilled in the art will appreciate that temporal filter 122 may use other methods as well.

In general, the lag histogram $LH(t_n, \tau)$ will have a "main peak", the location of which is near the instantaneous value of the fetal heart rate. The main peak of the lag histogram is the largest amplitude peak for which $\tau$ is greater than zero. The location of the main peak is referred to as $\tau_{lh}$, so that $LH(t_n, \tau_{lh})$ is the value of the amplitude of the main peak. Since the lag histogram is generated by temporally filtering the autocorrelation functions, and since the autocorrelation functions typically have peaks where $\tau$ equals the period of fetal heart rate, $\tau_{lh}$ is generally close to the instantaneous value of the fetal heart rate. When the fetal heart rate remains stable over a period of time, $\tau_{lh}$ will generally approach or become equal to the fetal heart rate. However since the fetal heart rate sometimes varies significantly from beat to beat and since the lag histogram is generated by temporal filter 122 which as discussed above has associated rise and fall times, the main peak may sometimes lag behind the instantaneous value of the fetal heart rate. The rate of change of the fetal heart rate, which can sometimes be as large as 28 beats per minute per beat, is sometimes too large for temporal filter 122 to quickly track. So when the fetal heart rate is changing rapidly, the main peak may lag behind the instantaneous value of the fetal heart rate, however, $\tau_{lh}$ will normally be within a given distance of the instantaneous value of the fetal heart rate. In other words, while the main peak may lag behind, it will generally not be far behind the instantaneous value of the fetal heart rate. In general, the absolute value of the difference between $\tau_{lh}$ and the instantaneous value of the fetal heart rate will normally be less than a constant value, the constant being related to the lag time associated with temporal filter 122 and to the maximum rate of change of the fetal heart rate (i.e., 28 beats per minute per beat). As will be discussed further below, system 100 uses this property of the lag histogram to stabilize the estimate of the fetal heart rate.

Figure 6:
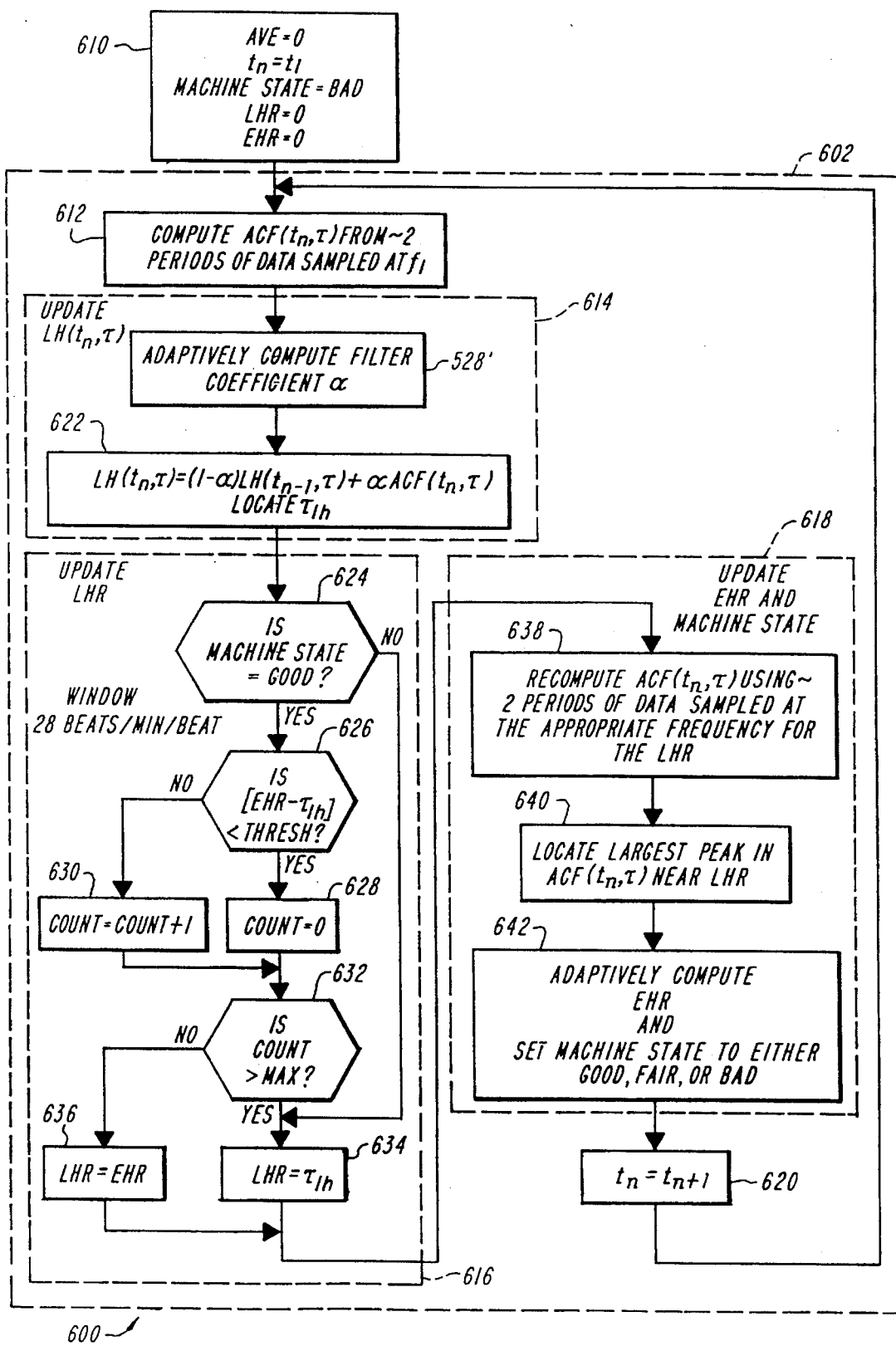
FIG. 6 shows a flow chart illustrating a method which may be used by fetal heart monitors constructed according to the invention for measuring the fetal heart rate.

FIG. 6 shows a flow chart illustrating one preferred method of operation 600 that system 100 (shown in FIG. 1) may use to measure the fetal heart rate. The first step in method 600 is an initialization step 610 during which the fundamental variables used in the method 600 are initialized. As in initialization step 510 (shown in FIG. 5) the variables AVE and $t_n$ are initialized to values of zero and $t_1$, respectively. Also in step 610, variables LHR and EHR are set to values of zero, and a variable known as "Machine State" is set to a state of "Bad". The variable LHR represents a value that is likely to be near the actual value of the fetal heart rate. This variable may be thought of as representing a "Likely Heart Rate". The variable EHR represents the estimated value of the fetal heart rate generated by system 100. This variable is used to generate the rate signal and may be thought of as representing an "Estimated Heart Rate". The variable Machine State represents the state of system 100. In the preferred mode of operation, system 100 may be thought of as having three possible states, Good, Fair, and Bad. When system 100 is in the Good state, there is a relatively high degree of confidence that the value of EHR is representative of the instantaneous value of the fetal heart rate. When system 100 is in the Fair state, there is a relatively low degree of confidence that the value of EHR is representative of the instantaneous value of the fetal heart rate, and when system 100 is in the Bad state, it is virtually certain that the value of EHR does not represent the instantaneous value of the fetal heart rate. Setting Machine State to Bad in step 610 represents that system 100 is presumed to be in a Bad state immediately after power up, or immediately after positioning ultrasound transducer 110 relative to the mother's abdomen.

Following initialization step 610, a computational step 612 is executed during which the autocorrelation function $ACF(t_n,\tau)$ is generated. Then an update step 614 is executed during which the lag histogram $LH(t_n,\tau)$ is generated. Following step 614, an update step 616 is executed during which the value of the likely heart rate LHR is updated. Then an update step 618 is executed during which the values of the estimated heart rate EHR and the Machine State are updated. After step 618, an incrementing step 620 is executed during which the value of the variable $t_n$ is incremented. Following step 620, step 612 and all succeeding steps are re-executed so that steps 612, 614, 616, 618, and 620 form a loop 602 which is repeatedly re-executed for as long as system 100 is in operation.

During step 612, autocorrelation function generator 120 generates the autocorrelation function $ACF(t_n,\tau)$. In the preferred embodiment, during step 612, rate estimator 124 adjusts the control signal so that autocorrelation function generator 120 generates the autocorrelation function $ACF(t_n,\tau)$ using the low resolution envelope signal. During step 614, temporal filter 122 then generates the lag histogram $LH(t_n,\tau)$ using this low resolution autocorrelation function $ACF(t_n,\tau)$. Since generating the autocorrelation function is relatively computationaly intensive, it is preferable to generate the autocorrelation function using the low resolution envelope signal, and then generate the lag histogram using this low resolution autocorrelation function. Using the low resolution signals in this manner decreases the time for one execution of loop 602 and thereby increases the speed of system 100. However, the higher resolution signals could of course be used in alternative methods according to the invention.

Step 614 is executed by sequentially executing a core step 528' and an update step 622. Core step 528' is similar to core step 528 (discussed in connection with FIG. 5), however step 528' preferably contains additional steps for considering the state of the system 100. In core step 528', the variable AVE is updated using steps 512, 514, and 516 (shown in FIG. 5) only when the variable Machine State equals Good or Fair. When the variable Machine State equals Bad, steps 512, 514, and 516 are skipped and the filter coefficient $\alpha$ is updated without first updating the value of AVE. This prevents the zero lag peaks from contributing to the value of AVE when system 100 is in a Bad state. In update step 622, temporal filter 122 generates the lag histogram $LH(t_n,\tau)$ using the filter coefficient $\alpha$ generated during core step 528'. Also during update step 622, filter 122 locates the main peak $LH(t_n, \tau_{lh})$ of the lag histogram.

In step 616, rate estimator 124 updates the value of the likely heart rate LHR. Step 616 includes decision steps 624, 626, update step 628, increment step 630, decision step 632, and update steps 634, 636. The first step in step 616 is decision step 624 during which the variable Machine State is examined to determine whether system 100 is in a Good state. If Machine State equals Good then decision step 626 is executed, and otherwise update step 634 is executed. During decision step 626, the most recently calculated value of the variable EHR is compared to $1/\tau_{lh}$. If the absolute value of the difference between EHR and $1/\tau_{lh}$ is less than a threshold THRESH, then EHR is said to be "close to" the main peak. If EHR is close to the main peak then update step 628 is executed and otherwise step 630 is executed. If step 628 is executed, the variable COUNT is set equal to zero, and if increment step 630 is executed, the variable COUNT is set equal to the previous value of COUNT plus unity. Following either of steps 628 or 630, decision step 632 is executed. During decision step 632 the variable COUNT is compared to a predefined variable MAX. If COUNT is greater than MAX, then step 634 is executed and otherwise step 636 is executed. If step 634 is executed, the value of LHR is set equal to $1/\tau_{lh}$ and if step 636 is executed, the value of LHR is set equal to the value of EHR.

In normal operation, rate estimator 124 executes step 616 so that update step 636 is executed and LHR is set equal to EHR. This corresponds to setting the value of the likely heart rate equal to the value of the estimated heart rate that was calculated by step 618 during the previous execution of loop 602. So during normal operation of system 100, the value of the likely heart rate LHR is set equal to the most recent value of the estimated heart rate EHR. This is desirable because during normal operation system 100 accurately estimates the instantaneous value of the heart rate and tracks any changes in the heart rate, and therefore, most of the time the best value for the likely heart rate LHR is the most recently calculated value of the estimated heart rate EHR. However, when conditions are such that there is only a low degree of confidence that the value of the estimated heart rate EHR actually corresponds to the fetal heart rate, then step 634 is executed and LHR is set equal to $1/\tau_{lh}$ which provides the best available estimate of the fetal heart rate.

As was stated above, most of the time the main peak of the lag histogram is within a given distance of the instantaneous value of the fetal heart rate. Decision step 626 therefore compares EHR to $1/\tau_{lh}$. When the absolute value of the difference between EHR and $1/\tau_{lh}$ is less than the threshold THRESH then it is likely that system 100 is accurately tracking the fetal heart rate, and the value of EHR is a good choice for LHR.

Sometimes, even when the absolute value of the difference between EHR and $1/\tau_{lh}$ is greater than the threshold THRESH, it is still likely that system 100 is accurately tracking the fetal heart rate. For example, when the fetal heart rate changes rapidly, it will take some time for the main peak of the lag histogram to track the change due to the lag delay of temporal filter 122. However, during the period that filter 122 takes to track the change, it is still likely that system 100 is accurately tracking the fetal heart rate. Therefore, even if the absolute value of the difference between EHR and $1/\tau_{lh}$ is greater than THRESH, step 636 will still be executed as long as COUNT is not greater than MAX. Those skilled in the art will appreciate that increment step 630 and decision step 632 form a delay timer, and as long as the absolute value of the difference between EHR and $1/\tau_{lh}$ is not greater than THRESH for a maximally allowable delay, step 636 will be executed and LHR will be set equal to EHR. However, when the absolute value of the difference between EHR and $1/\tau_{lh}$ remains greater than THRESH for longer than the maximally allowable delay, then it becomes apparent that system 100 is not tracking the fetal heart rate and it is unlikely that EHR is actually representative of the instantaneous value of the fetal heart rate. In this condition, step 634 is executed and the likely heart rate is set equal to $1/\tau_{lh}$ which provides the best possible guess of the actual value of the heart rate. $1/\tau_{lh}$ is unlikely to be equal to the instantaneous value of the fetal heart rate, however, $1/\tau_{lh}$ is likely to be close to it. One preferred choice for the value of MAX is to choose MAX so that the maximally allowable delay is about two seconds. A preferred choice for the threshold THRESH is about 20% of the heart rate, although this value can vary.

Another condition which causes execution of step 634 is when system 100 is not in a Good state. Decision step 624 examines the state of system 100, and if Machine State is not equal to Good, step 634 is next executed and LHR is set equal to $1/\tau_{lh}$. This represents that unless system 100 is in a Good state, it is unlikely that system 100 is accurately tracking the fetal heart rate. In this condition, EHR is unlikely to provide a good estimate of the fetal heart rate, so LHR is set equal to $1/\tau_{lh}$ which provides the best possible guess of the actual value of the fetal heart rate.

At the conclusion of step 616, when a value has been assigned to LHR, step 618 is executed during which the estimated heart rate EHR is calculated and the state of system 100 is measured. Step 618 is executed by sequentially executing steps 638, 640, and 642. In step 638, autocorrelation generator 120 regenerates the autocorrelation function $ACF(t_n,\tau)$ using one of the low, medium, and high resolution envelope signals and a data collection interval of approximately between two and three periods of data. Rate estimator 124 uses the value of the likely heart rate LHR to determine which of the envelope signals generator 120 will use and adjusts the control signal accordingly so that when LHR is near the top of the range (e.g., near 200 beats per minute) generator 120 uses the high resolution envelope signal, when LHR is near the middle of the range (e.g., near 100 beats per minute) generator 120 uses the medium resolution envelope signal, and when LHR is near the bottom of the range (e.g., near 50 beats per minute) generator 120 uses the low resolution envelope signal.

During step 640, rate estimator 124 locates the largest peak in the regenerated autocorrelation function $ACF(t_n,\tau)$ that is within a given distance, or window, of the likely heart rate LHR. The location of this peak is referred to as $\tau_{acf}$ and $ACF(t_n, \tau_{acf})$ is the value of the amplitude of the peak. Since in general, the actual instantaneous value of the fetal heart rate is unlikely to be very far from LHR, the size of the window is relatively small, and the size of the window is selected depending on the lag characteristic of temporal filter 122 and the maximum possible rate of change of a fetal heart. One preferred choice for the size of the window used in step 640 is 28 BPM. $\tau_{acf}$ may not be the location of the largest peak in the autocorrelation function, however other larger peaks which are further from LHR are normally indicative of noise. Rate estimator 124 thereby uses LHR to reject false peaks in the autocorrelation function and thereby stabilizes the determination of $\tau_{acf}$.

Following step 640, step 642 is executed during which rate estimator 124 generates the value of the estimated heart rate EHR, and updates the state of system 100. Rate estimator 122 also uses the variable EHR to generate the rate signal, and in one embodiment, estimator generates the rate signal so that at any point in time it is equal to the value of EHR. In one preferred embodiment, rate estimator 124 generates EHR using a single pole filter according to the formula shown in Equation (3)

$$EHR=(1-\beta)EHR+\beta\tau_{acf} \qquad (3)$$

in which $\beta$ is a filter coefficient which rate estimator 124 adaptively determines. So when rate estimator 124 uses Equation (3), estimator 124 generates the new value of EHR by summing $(1-\beta)$ times the old value of EHR and $\beta$ times $1/\tau_{acf}$. Rate estimator 124 may use many factors to determine the value of $\beta$ for any given execution of step 642. For example, rate estimator 124 may consider the departure of the zero lag peak from past zero lag peaks (i.e., the variable DEPARTURE discussed in connection with FIG. 5), and generate the filter coefficient $\beta$ so that it decreases as the departure increases. This is desirable since as discussed above, large departures indicate increased noise levels in the autocorrelation function, and when the noise level is high $\beta$ is preferably small so that the current value of $1/\tau_{acf}$ does not make a large contribution to the value of EHR. Rate estimator 124 may also consider the difference between the $1/\tau_{acf}$ and previous values of EHR and generate the filter coefficient $\beta$ so that it decreases as the distance between $1/\tau_{acf}$ and EHR increases. This is desirable since it is unlikely that the fetal heart rate will change by large amounts in a short amount of time, so when the current value of $1/\tau_{acf}$ is greatly different than the value of EHR it is likely that the current value of $1/\tau_{acf}$ is representative of noise and should therefore make only a relatively small contribution to the new value of EHR. Rate estimator may further consider the strength of the peak in the autocorrelation function $ACF(t_n, \tau_{acf})$ in comparison to the zero lag peak $ACF(t_n, 0)$. Rate estimator preferably generates the filter coefficient $\beta$ so that it increases as the strength of $ACF(t_n, \tau_{acf})$ increases in comparison to the zero lag peak. Rate estimator may also consider the size of the zero lag peak and generate the filter coefficient $\beta$ so that it decreases or is very small when the zero lag peak is greater than a threshold, since large values of the zero lag peak indicate that the autocorrelation function is representative of noise. Rate estimator 124 preferably uses these same considerations for updating the state of system 100. All the considerations that favor increasing the filter coefficient $\beta$ favor setting the variable Machine State to Good, and all the considerations that favor decreasing the filter coefficient $\beta$ favor setting the variable Machine State to Bad.

In operation, the state of the machine is a function of a variable representing the assumed quality of the measurement (Q) having a value between some minimum (for example, zero) and some maximum value (M). There exist two thresholds between the minimum (zero) and the maximum value (M) such that:

$$0 < BF < FG < M \qquad (4)$$

The threshold BF in the above inequality statement (4) refers to the threshold between BAD and FAIR. The threshold FG refers to the threshold between FAIR and GOOD. Depending upon the value of the variable Q in relation to the above thresholds determines the state of the machine. The following table applies:

| STATE | Value of Q |
|-------|------------|
| BAD   | Q < BF     |
| FAIR  | Q > BF, Q < FG |
| GOOD  | Q > FG     |

The variable Q is updated based upon the estimated confidence in the measurement. The confidence in the measurement is based upon several factors, all of which are present in the adaptive filter coefficient $\beta$ as described above. Therefore it is possible to use the value of $\beta$ to update the variable Q. If the confidence is greater than a certain value, then the value of Q is increased by a value based upon a factor of the confidence. If the confidence is less than a certain value, the variable Q is decreased by a value based upon a factor of the lack of confidence. The variable Q may not assume values less than the minimum or maximum values as stated above. This prevents the machine state from assuming very large values of either confidence or lack of confidence.

Fetal monitor 100 has been discussed in terms of being implemented using discrete functional components, such as for example, autocorrelation function generator 120, filter 122, and estimator 124. Those skilled in the art will appreciate that system 100 may be implemented in may different ways. For example, each functional component may be implemented as a discrete component using dedicated circuitry, or alternatively, some of the components may be implemented as software modules running on a digital computer. Further, many of the components may be implemented using standard digital signal processing circuitry that is controlled by software. The digital signal processing circuitry may also be time shared so that more than one functional component is implemented using the same digital signal processing circuitry.

Fetal monitor 100 has also been discussed in terms of generating a sequence of autocorrelation functions (e.g., $ACF(t_1, \tau)$, $ACF(t_2, \tau)$), and a sequence of lag histograms (e.g., $LH(t_1, \tau)$, $LH(t_2, \tau)$). Those skilled in the art will appreciate that the autocorrelation and lag histograms may alternatively be generated as a continuous time varying signals rather than at discrete time intervals. In this mode, at any point in time, the autocorrelation function is representative of the autocorrelation function of a corresponding portion of the envelope signal, and at any point in time, the lag histogram may be generated by filtering (e.g., temporally averaging) the autocorrelation function over a corresponding time interval. Further, while fetal monitor 100 has been discussed in terms of a digital system using data sampler 114, in alternative embodiments monitors constructed according to the invention may eliminate data sampler 114 and instead process continuous analog signals, so that the autocorrelation function and/or the lag histogram may be generated as continuous analog signals.

The use of the lag histogram has been discussed in connection with fetal monitor 100, however, those skilled in the art will appreciate that the lag histogram may be used in systems for measuring the period of any type of periodic or quasi-periodic signal. In general, using the lag histogram to stabilize the determination of rate from the autocorrelation function is an effective strategy. Whereas the autocorrelation function is responsive to short term variability when it is generated using an appropriately small data collection interval, it is also highly sensitive to noise. Using the main peak of the lag histogram to limit the search for peaks in the autocorrelation function stabilizes the determination of rate and is more effective than locating the peaks of the autocorrelation function directly and then using ad hoc techniques to compensate for the shortcomings of the autocorrelation function as is typically done in the prior art.

Further, as described, the lag histogram was generated by temporally filtering the entire autocorrelation function. In other forms of the invention, the lag histogram may be generated by temporally filtering only portions of the autocorrelation function, for example, only the peaks of the autocorrelation function, or only portions of the autocorrelation function that are greater than a threshold. Also, the lag histogram may be generated using a different granularity than that of the autocorrelation function (i.e., the lag histogram may be quantized into bins along the $\tau$ axis and the size of the bins need not match the quantization interval used for the autocorrelation function). In each bin, the lag histogram is generated by temporally filtering a corresponding portion of the autocorrelation function.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A system for measuring the periodic content of an input signal, comprising:

(A) autocorrelation means, responsive to the input signal, for generating a sequence of autocorrelation functions, each of the autocorrelation functions in the sequence being representative of an autocorrelation function of a portion of the input signal; and (B) temporal filter means for temporally filtering the autocorrelation functions to generate a lag histogram.

2. A system according to claim 1, wherein the temporal filter means comprises a single pole filter.

3. A system according to claim 1, wherein the temporal filter includes means for generating a sequence of lag histograms.

4. A system according to claim 1, wherein the temporal filter means includes means for generating a scaled correlation signal by multiplying one of the autocorrelation functions by a filter coefficient.

5. A system according to claim 4, wherein the temporal filter means includes means for generating a scaled lag signal by multiplying the lag histogram by one minus the filter coefficient.

6. A system according to claim 5, wherein the temporal filter means generates the lag histogram by summing the scaled correlation signal and the scaled lag signal.

7. A system according to claim 6, further including means for adaptively varying the filter coefficient.

8. A system according to claim 6, wherein each of the autocorrelation functions is characterized by a zero lag peak, and further including means for adaptively varying the filter coefficient as a function of the zero lag peaks.

9. A system according to claim 1, further including means for locating a main peak in the lag histogram.

10. A system according to claim 9, further including means for locating a peak in one of the autocorrelation functions that is within a threshold distance of the main peak in the lag histogram.

11. A fetal heart rate monitor for measuring the heart rate of a fetus, comprising:

(A) means for generating an ultrasound signal that propagates into the fetus;

(B) means for receiving an ultrasound reflection signal reflected by the fetus and means for converting the ultrasound reflection signal to an electrical signal;

(C) autocorrelation means, responsive to the electric signal, for generating a sequence of autocorrelation functions, each of the autocorrelation functions in the sequence being representative of an autocorrelation function of a portion of the electric signal; and (D) temporal filter means for temporally filtering the autocorrelation functions to generate a lag histogram.

12. A fetal heart rate monitor according to claim 11, further including means for sampling the electrical signal at a sampling frequency and thereby generating a sampled signal.

13. A fetal heart monitor according to claim 12, further including band pass filter means for filtering the sampled signal and thereby generating a filtered signal.

14. A fetal heart monitor according to claim 13, wherein the autocorrelation means includes means for receiving the filtered signal and generating therefrom a rectified signal, each portion of the rectified signal being equal to an absolute value of a corresponding portion of the filtered signal.

15. A fetal heart monitor according to claim 14, wherein the autocorrelation means further includes means for generating a transform signal representative of a Fourier transform of the rectified signal.

16. A fetal heart monitor according to claim 15, further including means for multiplying the transform signal by a conjugate signal and thereby generating a frequency correlation signal.

17. A fetal heart monitor according to claim 16, further including means for filtering the frequency correlation signal and thereby generating a filtered frequency signal.

18. A fetal heart monitor according to claim 17, further including means for generating one of the autocorrelation functions by generating a signal representative of an inverse Fourier transform of the filtered frequency signal.

19. A fetal heart monitor according to claim 11, further including means for locating a main peak in the lag histogram.

20. A system according to claim 19, further including means for locating a peak in one of the autocorrelation functions that is within a threshold distance of the main peak in the lag histogram.

21. A fetal heart rate monitor according to claim 11, further including means for sampling the electrical signal at a plurality of sampling frequencies and thereby generating a plurality of sampled signals.

22. A fetal heart monitor according to claim 11, further including means for sampling the electrical signal at first, second, and third sampling frequencies and thereby generating first, second, and third sampled signals.

23. A fetal heart monitor according to claim 22, further including band pass filter means for filtering the first, second, and third sampled signals, and thereby generating first, second, and third filtered signals, respectively.

24. A system for measuring the periodic content of an input signal, comprising:

(A) autocorrelation means, responsive to the input signal, for generating an autocorrelation function, at any point in time the autocorrelation function being representative of an autocorrelation function of a portion of the input signal; and (B) lag histogram means for generating a lag histogram from the autocorrelation function, the lag histogram means including means for suppressing transitory features in the autocorrelation function so that said transitory features make a relatively small contribution to the lag histogram and means for emphasizing temporally consistent features of the autocorrelation function so that said temporally consistent features make a relatively large contribution to the lag histogram.

25. A system for measuring the periodic content of an input signal, comprising:

(A) autocorrelation means, responsive to the input signal, for generating an autocorrelation function, at any point in time the autocorrelation function being representative of an autocorrelation function of a portion of the input signal; and (B) temporal filter means for temporally filtering portions of the autocorrelation function to generate a lag histogram.

* * * * *